US008221759B2

(12) United States Patent
Pilkington et al.

(10) Patent No.: US 8,221,759 B2
(45) Date of Patent: Jul. 17, 2012

(54) NEUTRALIZING MONOCLONAL ANTIBODIES TO RESPIRATORY SYNCYTIAL VIRUS

(75) Inventors: Glenn R. Pilkington, Bethesda, MD (US); Page S. Gilmour, Rockville, MD (US); Robert M. Chanock, Betheseda, MD (US); James E. Crowe, Jr., Brentwood, TN (US); Brian R. Murphy, Bethesda, MD (US)

(73) Assignee: Intracel Resources LLC, Frederick, MD (US)

( * ) Notice: Subject to any disclaimer, the term of this patent is extended or adjusted under 35 U.S.C. 154(b) by 0 days.

(21) Appl. No.: 13/250,357

(22) Filed: Sep. 30, 2011

(65) Prior Publication Data

US 2012/0087909 A1    Apr. 12, 2012

Related U.S. Application Data

(60) Division of application No. 12/082,000, filed on Apr. 24, 2008, now abandoned, which is a division of application No. 10/425,855, filed on Apr. 30, 2003, now Pat. No. 7,488,477, which is a continuation of application No. 09/043,530, filed as application No. PCT/US96/14937 on Sep. 18, 1996, now abandoned.

(60) Provisional application No. 60/003,931, filed on Sep. 18, 1995.

(51) Int. Cl.
*A61K 39/42* (2006.01)
(52) U.S. Cl. ............... 424/147.1; 424/133.1; 424/135.1; 424/141.1; 530/388.1; 530/388.2; 530/388.3
(58) Field of Classification Search ........................ None
See application file for complete search history.

(56) References Cited

U.S. PATENT DOCUMENTS

| 4,800,078 A | 1/1989 | Prince et al. |
| 4,946,778 A | 8/1990 | Ladner et al. |

FOREIGN PATENT DOCUMENTS

| WO | WO 92/04381 | 3/1992 |
| WO | WO 93/20210 | 10/1993 |
| WO | WO 94/06448 | 3/1994 |
| WO | WO 94/17105 | 8/1994 |
| WO | WO 95/03832 | 2/1995 |
| WO | WO 95/04081 | 2/1995 |

OTHER PUBLICATIONS

Barbas, et al., "Assembly of Combinatorial Antibody Libraries on Phage Surfaces: The Gene III Site", Proc. Natl. Acad. Sci. (USA), 1991, 88:7978-7982.
Barbas et al., "Human Monoclonal Fab Fragments Derived From a Combinatorial Library Bind to Respiratory Syncytial Virus F. Glycoprotein and Neutralize Infectivity", Proc. Natl. Acad. Sci. (USA), 1992, 89:10164-10168.
Better et al., "*Escherichia coli* Secretion of an Active Chimeric Antibody Fragment" Science, 1988, 240:1041-1043.
Burton et al., "Efficient Neutralization of Primary Isolates of HIV-1 by a Recombinant Human Monoclonal Antibody", Science, 1994, 266:1024-1027.
Burton et al., "A Large Array of Human Monoclonal Antibodies to Type 1 Human Immunodeficiency Virus From Combinatorial Libraries of Asymptomatic Seropositive Individuals", Proc. Natl. Acad. Sci. (USA), 1991, 88:10134-10137.
Clackson et al., "Making Antibody Fragments Using Phage Display Libraries", Nature, 1991, 352:624-628.
Clark, William R., "The Experimental Foundations of Modern Immunology, 3rd Ed.", John Wiley & Sons, 1986.
Coates et al., "An Antigenic Analysis of Respiratory Syncytial Virus Isolates by a Plaque Reduction Neutralization Test", American Journal of Epidemiology, 1966, 83(2):299-313.
Duan et al., "Potent Inhibition of Human Immunodeficiency Virus Type 1 Replication by an Intracellular Anti-Rev Single-chain Antibody", Proc. Natl. Acad. Sci. (USA), 1994, 91:5075-5079.
Gold et al., "Translational Initiation in Prokaryotes", Rev. Microbiol., 1981, 35:365-403.
Greenspan et al., "Defining Epitopes: Not as Easy as it Seems", Nature Biotechnology, 1999, 17: 936-937.
Guarente et al., "Improved Methods for Maximizing Expression of a Cloned Gene: a Bacterium That Synthesizes Rabbit β-Globin", Cell, 1980 20:543-553.
Guarente et al., "A Technique for Expressing Eukaryotic Genes in Bacteria", Science, 1980, 209:1428-1430.
Hemming et al., "Intravenous Immunoglobulin Treatment of Respiratory Syncytial Virus Infections in Infants and Young Children", Antimicrob. Agnts. Chemotherap., 1987, 31(12): 1882-1886.
Hemming et al., "Studies of Passive Immunotherapy for Infections of Respiratory Syncytial Virus in the Respiratory Tract of a Primate Model", J. Inf. Dis., 1985, 152:1083-1087.
Herlyn et al., "Anti-Idiotypic Antibodies Bear the Internal Image of a Human Tumor Antigen", Science, 1986, 232:100-102.
Huse et al., "Generation of a Large Combinatorial Library of the Immunoglobulin Repertoire in Phage Lambda", Science, 1989, 246:1275-1281.
Jones et al., "Replacing the Complementarity-determining Regions in a Human Antibody With Those From a Mouse", Nature 1986, 321:522-525.
Kang et al., "Combinatorial Immunoglobulin Libraries in Phage λ", Methods: A Companion to Methods in Enzymology, 1991, 2(a):111-118.

(Continued)

*Primary Examiner* — Robert A Zeman
(74) *Attorney, Agent, or Firm* — Dickstein Shapiro LLP

(57) ABSTRACT

The present invention relates to the identification and cloning of a novel neutralizing human monoclonal antibody to the Respiratory Syncytial Virus. The invention provides such antibodies, fragments of such antibodies retaining RSV-binding ability, chimeric antibodies retaining RSV-binding ability, and pharmaceutical compositions including such antibodies. The invention further provides for isolated nucleic acids encoding the antibodies of the invention and host cells transformed therewith. Finally, the invention provides for diagnostic and therapeutic methods employing the antibodies and nucleic acids of the invention.

1 Claim, No Drawings

OTHER PUBLICATIONS

Köhler et al., "Continuous Cultures of Fused Cells Secreting Antibody of Predefined Specificity", Nature, 1997, 256:495-497.

Lai et al., "Conserved Organization of the Human and Murine T-Cell Receptor β-gene Families", Division of Biology 147-75, Letters to Nature, 1988, 331:543-546.

Marasco et al., "Design, Intracellular Expression, and Activity of a Human Anti-human Immunodeficiency Virus Type 1 gp120 Single-chain Antibody", Proc. Natl. Acad. Sci. (USA), 1993, 90:7889-7893.

Marks et al., "By-passing Immunization Human Antibodies from V-gene Libraries Displayed on Phage", J. Mol. Biol., 1991, 222:581-597.

McIntosh et al., "Respiratory Syncytial Virus", Virology, 2nd ed., 1990, 38:1045-1072.

Mullinax et al., "Identification of Human Antibody Fragment Clones Specific for Tetanus Toxoid in a Bacteriophage λ Immunoexpression Library", Proc. Acad. Sci. (USA), 1990, 87:8095-8099.

Murphy et al., "Enhanced Pulmonary Histophathology is Observed in Cotton Rats Immunized With Formalin-inactivated Respiratory Syncytal Virus (RSV) or Purified F Glycoprotein and Challenged With RSV 3-6 Months After Immunization", Vaccine, 1990, 8:497-502.

Ogilvie et al., "Maternal Antibody and Respiratory Syncytial Virus Infection in Infancy", J. Med. Virol., 1981, 7:263-271.

Oliver, Donald B., "Periplasm and Protein Secretion", *Escherichia coli* and *Salmonella typhimurium* Cellular and Molecular Biology, American Society for Microbiology, 1987, 1:56-69.

Prince et al., "The Pathogenesis of Respiratory Syncytial Virus Infection in Cotton Rats", Am. Assoc. of Path., 1978, 93:771-792.

Prince et al., "Quantitative Aspects of Passive Immunity to Respiratory Syncytial Virus Infection in Infant Cotton Rats", J. Virol., 1985, 55:517-520.

Prince et al., "Effectiveness of Topically Administered Neutralizing Antibodies in Experimental Immunotherapy of Respiratory Syncytial Virus Infection in Cotton Rats", J Virol., 1987, 691(6):1851-1854.

Prince et al., "Immunoprophylaxis and Immunotherapy of Respiratory Syncytial Virus Infection in the Cotton Rat", Virus Research, 1985, 3:193-206.

Roberts et al., "A General Method for Maximizing the Expression of a Cloned Gene", Proc. Natl. Acad. Sci. (USA), 1979, 76(2):760-764.

Roberts et al., "Synthesis of Simian Virus 40 t Antigen in *Escherichia coli*", Proc. Natl. Acad. Sci. (USA), 1979, 76(11):5596-5600.

Roberts et al., "Directed Evolution of a Protein: Selection of Potent Neutrophil Elastase Inhibitors Displayed on M13 Fusion Phage" Proc. Natl. Acad. Sci (USA), 1992, 89:2429-2433.

Roitt, Ivan M., "Essential Immunology", 7th Ed. (Blackwell Scientific Publications), 1991.

Sambrook et al., "Molecular Cloning: A Laboratory Manual, 2nd Ed.", 11-38, 1989.

Sastry et al., "Cloning of the Immunological Repertoire in *Escherichia coli* for Generation of Monoclonal Catalytic Antibodies: Construction of a Heavy Chain Variable Region-specific cDNA Library", Proc. Natl. Acad. Sci. (USA), 1989, 86:5728-5732.

Sciarra et al., "Aerosols", Remington's Pharmaceutical Sciences, 1990, 92:1694-1712.

Shine et al., "Determinant of Cistron Specificity in Bacterial Ribosomes", Nature, 1975, 254:34-38.

Smith et al., "Filamentous Fusion Phage: Novel Expression Vectors that Display Cloned Antigens on the Virion Surface, Science, 1985, 228:1315-1317.

Taniguchi et al., "Site-directed Mutations in the Initiator Region of the Bacteriophage Qβ Coat Cistron and Their Effect on Ribosome Binding", J. Mol. Biol., 1978, 118:533-565.

Taylor et al., "Monoclonal Antibodies Protect Against Respiratory Syncytial Virus Infection in Mice", Immunology, 1984, 52:137-142.

Tempest et al., "Reshaping a Human Monoclonal Antibody to Inhibit Human Respiratory Syncytial Virus Infection in Vivo", Bio/Technololgy, 1991, 9:266-271.

Verhoeyen et al., "Reshaping Human Antibodies: Grafting an Antilysozyme Activity", Science, 1988, 39: 1534-1536.

Walsh et al., "Analysis of the Respiratory Syncytial Virus Fusion Protein Using Monoclonal and Polyclonal Antibodies", J. Gen. Virology, 1986, 67:505-513.

Walsh et al., "Protection From Respiratory Syncytial Virus Infection in Cotton Rats by Passive Transfer of Monoclonal Antibodies", Infection and Immunity, 1984, 43(2):756-758.

Walsh et al., "Purification and Characterization of GP90, One of the Envelope Glycoproteins of Respiratory Syncytial Virus", J. Gen. Virol., 1984, 65:761-767.

Walsh et al., "Purification and Characterization of the Respiratory Syncytial Virus Fusion Protein", J. Gen. Virol., 1985, 66:409-415.

Ward et al., "Binding Activities of a Repertoire of Single Immunoglobulin Variable Domains Secreted From *Escherichia coli*", Nature, 1989, 341:544-546.

Whittle et al., "Expression of COS Cells of a Mouse-human Chimaeric B72.3 Antibody", Protein Eng., 1987, 1:499-505.

SEQUENCE LISTING

<160> NUMBER OF SEQ ID NOS: 22

<210> SEQ ID NO 1
<211> LENGTH: 123
<212> TYPE: PRT
<213> ORGANISM: Homo sapiens

<400> SEQUENCE: 1

```
Leu Glu Glu Ser Gly Gly Asp Leu Val Gln Pro Gly Arg Ser Leu Arg
 1               5                  10                  15

Leu Ser Cys Ser Thr Ser Gly Phe Ser Phe Gly Asp Tyr Pro Val Asn
            20                  25                  30

Trp Phe Arg Gln Ala Pro Gly Lys Gly Leu Glu Trp Leu Gly Ile Val
        35                  40                  45

Arg Ser Arg Leu Tyr Gly Gly Thr Leu Gln Tyr Ala Ala Ser Val Glu
    50                  55                  60

Gly Arg Phe Thr Ile Ser Arg Asp Asp Ser Lys Ser Ile Ala Tyr Leu
65                  70                  75                  80
```

```
His Met Asn Ser Leu Lys Ser Glu Asp Thr Ala Val Tyr Tyr Cys Gly
            85                  90                  95

Val Pro Val Ala Asn Ile Asp Tyr Trp Gly Gln Gly Thr Leu Val Thr
            100                 105                 110

Val Ser Ser Ala Ser Thr Lys Gly Pro Ser Ser
        115                 120

<210> SEQ ID NO 2
<211> LENGTH: 27
<212> TYPE: PRT
<213> ORGANISM: Homo sapiens

<400> SEQUENCE: 2

Leu Glu Glu Ser Gly Gly Asp Leu Val Gln Pro Gly Arg Ser Leu Arg
1               5                   10                  15

Leu Ser Cys Ser Thr Ser Gly Phe Ser Phe Gly
            20                  25

<210> SEQ ID NO 3
<211> LENGTH: 5
<212> TYPE: PRT
<213> ORGANISM: Homo sapiens

<400> SEQUENCE: 3

Asp Tyr Pro Val Asn
1               5

<210> SEQ ID NO 4
<211> LENGTH: 14
<212> TYPE: PRT
<213> ORGANISM: Homo sapiens

<400> SEQUENCE: 4

Trp Phe Arg Gln Ala Pro Gly Lys Gly Leu Glu Trp Leu Gly
1               5                   10

<210> SEQ ID NO 5
<211> LENGTH: 19
<212> TYPE: PRT
<213> ORGANISM: Homo sapiens

<400> SEQUENCE: 5

Ile Val Arg Ser Arg Leu Tyr Gly Gly Thr Leu Gln Tyr Ala Ala Ser
1               5                   10                  15

Val Glu Gly

<210> SEQ ID NO 6
<211> LENGTH: 32
<212> TYPE: PRT
<213> ORGANISM: Homo sapiens

<400> SEQUENCE: 6

Arg Phe Thr Ile Ser Arg Asp Asp Ser Lys Ser Ile Ala Tyr Leu His
1               5                   10                  15

Met Asn Ser Leu Lys Ser Glu Asp Thr Ala Val Tyr Tyr Cys Gly Val
            20                  25                  30

<210> SEQ ID NO 7
<211> LENGTH: 7
<212> TYPE: PRT
<213> ORGANISM: Homo sapiens

<400> SEQUENCE: 7
```

Pro Val Ala Asn Ile Asp Tyr
1               5

<210> SEQ ID NO 8
<211> LENGTH: 19
<212> TYPE: PRT
<213> ORGANISM: Homo sapiens

<400> SEQUENCE: 8

Trp Gly Gln Gly Thr Leu Val Thr Val Ser Ser Ala Ser Thr Lys Gly
1               5                   10                  15

Pro Ser Ser

<210> SEQ ID NO 9
<211> LENGTH: 109
<212> TYPE: PRT
<213> ORGANISM: Homo sapiens

<400> SEQUENCE: 9

Leu Thr Gln Pro His Ser Val Ser Glu Ser Leu Gly Lys Thr Val Thr
1               5                   10                  15

Ile Ser Cys Thr Arg Ala Gly Gly Arg Ile Ala Ser Asn Tyr Val Gln
            20                  25                  30

Trp Tyr Gln Gln Arg Pro Gly Ser Ser Pro Thr Thr Val Ile Tyr Glu
        35                  40                  45

Asp Asn Gln Arg Pro Phe Gly Val Pro Asp Arg Phe Ser Gly Ser Ile
    50                  55                  60

Asp Thr Ser Ser Asn Ser Ala Ser Leu Thr Ile Ser Gly Leu Lys Thr
65                  70                  75                  80

Glu Asp Glu Ala Asp Tyr Tyr Cys Gln Ser Tyr Asp Ser Glu Asn Pro
                85                  90                  95

Trp Val Phe Gly Gly Gly Thr Lys Leu Thr Val Leu Gly
            100                 105

<210> SEQ ID NO 10
<211> LENGTH: 19
<212> TYPE: PRT
<213> ORGANISM: Homo sapiens

<400> SEQUENCE: 10

Leu Thr Gln Pro His Ser Val Ser Glu Ser Leu Gly Lys Thr Val Thr
1               5                   10                  15

Ile Ser Cys

<210> SEQ ID NO 11
<211> LENGTH: 13
<212> TYPE: PRT
<213> ORGANISM: Homo sapiens

<400> SEQUENCE: 11

Thr Arg Ala Gly Gly Arg Ile Ala Ser Asn Tyr Val Gln
1               5                   10

<210> SEQ ID NO 12
<211> LENGTH: 15
<212> TYPE: PRT
<213> ORGANISM: Homo sapiens

<400> SEQUENCE: 12

Trp Tyr Gln Gln Arg Pro Gly Ser Ser Pro Thr Thr Val Ile Tyr
1               5                   10                  15

<210> SEQ ID NO 13
<211> LENGTH: 7
<212> TYPE: PRT
<213> ORGANISM: Homo sapiens

<400> SEQUENCE: 13

Glu Asp Asn Gln Arg Pro Phe
 1               5

<210> SEQ ID NO 14
<211> LENGTH: 34
<212> TYPE: PRT
<213> ORGANISM: Homo sapiens

<400> SEQUENCE: 14

Gly Val Pro Asp Arg Phe Ser Gly Ser Ile Asp Thr Ser Ser Asn Ser
 1               5                  10                  15

Ala Ser Leu Thr Ile Ser Gly Leu Lys Thr Glu Asp Glu Ala Asp Tyr
            20                  25                  30

Tyr Cys

<210> SEQ ID NO 15
<211> LENGTH: 10
<212> TYPE: PRT
<213> ORGANISM: Homo sapiens

<400> SEQUENCE: 15

Gln Ser Tyr Asp Ser Glu Asn Pro Trp Val
 1               5                  10

<210> SEQ ID NO 16
<211> LENGTH: 11
<212> TYPE: PRT
<213> ORGANISM: Homo sapiens

<400> SEQUENCE: 16

Phe Gly Gly Gly Thr Lys Leu Thr Val Leu Gly
 1               5                  10

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
attaaccctc actaaag                                                    17

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gaattctaaa ctagctagtc g                                               21

<210> SEQ ID NO 19
<211> LENGTH: 18
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 19
gaagtagtcc ttgaccag                                                    18

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gaagtcactt atgagacaca c                                                21

<210> SEQ ID NO 21
<211> LENGTH: 369
<212> TYPE: DNA
<213> ORGANISM: Homo sapiens

<400> SEQUENCE: 21
ctcgaggagt ctgggggaga cttggtacag ccagggcggt ccctgagact ctcctgttca      60
acttcaggat tcagttttgg tgactatcct gtgaattggt tccgccaggc tccagggaag     120
gggctggagt ggctaggtat cgttagaagc agactttatg gtgggacact tcaatacgcc     180
gcgtctgtgg aaggcagatt caccatctca agagatgatt ccaaaagcat cgcctatctg     240
cacatgaaca gtctgaaatc cgaggacacg gccgtgtatt attgtggtgt accagtggct     300
aacattgact actggggcca gggaaccctg gtcaccgtct cttcagcctc caccaagggt     360
ccatcgtct                                                            369

<210> SEQ ID NO 22
<211> LENGTH: 330
<212> TYPE: DNA
<213> ORGANISM: Homo sapiens

<400> SEQUENCE: 22
gagctcactc agccccactc tgtgtcggag tctctgggga agacggtaac catctcctgc      60
acccgcgccg gtggcagaat tgccagcaac tatgtgcagt ggtaccagca gcgcccgggc     120
agttccccca ccactgtgat ttatgaggat aaccaaagac cctttggggt ccctgatcgg     180
ttctctggct ccatcgacac ctcctccaac tctgcctccc tcaccatctc tggactgaag     240
actgaggacg aggctgacta ctactgtcag tcttatgata gcgaaaaccc ttgggtgttc     300
ggcgggggga ccaagctgac cgtcctaggt                                     330
```

NEUTRALIZING MONOCLONAL ANTIBODIES TO RESPIRATORY SYNCYTIAL VIRUS

CROSS REFERENCE TO RELATED APPLICATIONS

This is a divisional application of U.S. application Ser. No. 12/082,000, filed Apr. 24, 2008, now abandoned which is a divisional application of U.S. application Ser. No. 10/425,855, filed Apr. 30, 2003, now U.S. Pat. No. 7,488,477, which is a continuation application (and claims the benefit of priority under 35 U.S.C. §120) of U.S. application Ser. No. 09/043,530, filed Oct. 9, 1998 now abandoned, which is a national stage application (under 35 U.S.C. §371) of and claims priority to PCT Application No. PCT/US96/14937, Sep. 18, 1996, which claims priority from U.S. provisional application Ser. No. 60/003,931, Sep. 18, 1995. The disclosures of the prior applications are considered part of (and are incorporated by reference in) the disclosure of this application.

SEQUENCE LISTING

The instant application contains a Sequence Listing which has been submitted in ASCII format via EFS-Web and is hereby incorporated by reference in its entirety.

FIELD OF THE INVENTION

This invention relates generally to the field of immunology and specifically to monoclonal antibodies which bind to and neutralize respiratory syncytial virus (RSV).

BACKGROUND OF THE INVENTION

RSV represents a major health problem, worldwide. In the United States alone, there are currently approximately 250,000 newborn infants and children per year who may develop severe or fatal RSV disease. RSV is the major viral cause of severe pediatric lower respiratory tract diseases, such as pneumonia and bronchiolitis, worldwide. It also results in a high rate of morbidity and mortality in infants or young children with cardiopulmonary disease or an immunodeficiency.

In addition to the childhood population at risk (McIntosh and Chanock (1990) *Virology*, 2nd edn. (Fields and Knipe, eds) Raven Press, Ltd., New York, pp. 1045-1072), there is a considerable and increasingly large population of immunosuppressed adults at risk due to the increasingly widespread application of organ transplant, cancer/leukemia therapies such as bone marrow transplantation and the proliferation of HIV infections in the homosexual population. HIV is now the leading killer of homosexuals in the 25-40 year age group, in the U.S.A. The aged, who represent a growing population in developing countries, also are at risk due to immune deficiencies resulting from their aging immune systems, and RSV can be endemic in nursing home populations, particularly during the Winter season.

Whilst antibiotic therapy of bacterial infection has been successful in many diseases, few antibiotics are available for therapy of viral infections and none are currently available for effective treatment of RSV infection. However the severity of viral infections is usually also correlated with the immune status of the patient. For example, there is a correlation between levels of maternal IgG antibodies to RSV and the resistance of infants to infection during the first months of life, when the risk of severe disease is greatest (Ogilvie, et al., *J. Med. Virol.* 7:263, 1981). Pooled human gamma globulin with high titer RSV neutralizing antibodies or RSV neutralizing murine monoclonal antibodies can protect small animals from pulmonary infection with RSV and, when administered therapeutically, can be effective in small animals and primates at the height of RSV infection (Walsh, et al., *Infection and Immunity*, 43:756, 1984; Prince, et al., *J. Virol.*, 55:517, 1985; Prince, et al., *Virus Research*, 3:193, 1985 Prince, et al., *J. Virol.*, 61:1851, 1987; Herruning, et al., *J. Inf. Dis.*, 152: 1083, 1985). Pooled human IgG containing RSV neutralizing antibodies has also been used clinically, to therapeutic effect, in a study of serious RSV disease in infants and young children (Hemming, et al., *Antimicrob. Agnts. Chemotherap.*, 31: 1882, 1987). However the use of pooled human sera for the treatment of RSV infection has several drawbacks. Availability is limited. Batches are not reproducible. Titers are 100 to 1,000 fold lower than for monoclonal antibody titers and the risk of iatrogenic infection is always present when using human serum, due to the variable resistance of microorganisms to the sterilization procedures utilized.

An RSV vaccine for active immunization, if available, could not be utilized for the treatment of newborn babies with immature immune systems or patients who are immunosuppressed. In patients where prophylactic passive immunotherapy is required, as a result of a more chronic form of disease, current therapy is mediated via periodic intravenous inoculation of human IgG prepared from pooled plasma. This type of therapy, due to the low titers of neutralizing anti-RSV antibodies, involves a large quantity of globulin (e.g., 0.75 gm per kg) and consequently requires administration intravenously, in a clinic or hospital, over a lengthy period (2 to 4 hours), on a monthly basis during the high risk months (fall, winter and early spring).

The neutralizing component of human anti-RSV antibody preparations, derived from pooled human plasma, is only a minor fraction of the total antibody present. The development of mouse monoclonal antibody technology thus provided cloned neutralizing antibodies of greater specific activity than the pooled human plasma preparations. However problems resulting from immune responses to the mouse antibodies, in human patients, have precluded the general application of these preparations for passive immunotherapy in humans. The development of human monoclonal antibodies to RSV has been thwarted, until recently, by the unsuccessful adaptation of monoclonal technology to the human system. Human hybridomas and immortalized EBV transformed B-lymphoblastoid cell lines, as well as mouse/human hybridomas are generally unstable antibody producers, even after multiple cloning steps. The cloning and expression of human monoclonal antibodies, in *E. coli* utilizing phage (Huse et al., *Science* 246: 1275-1281, 1989; Clackson et al., *Nature* 352: 624-628, 1991; Barbas et al., *Proc. Natl. Acad. Sci.* (USA): 88:7978-7982, 1991), has obviated this problem. RSV-specific human monoclonal antibody is now available with a 100 to 1000-fold higher concentration of specific antibody than pooled plasma preparations. The use of these human monoclonal antibody preparations will correspondingly decrease the volume of antibody preparations required for prophylaxis or therapy by the same order of magnitude. Effective doses of monoclonal antibody may now be administered intramuscularly (i.m.), thereby reducing the period of time required. Prophylaxis in new born babies or infants can now be performed at home, as opposed to in the clinic or hospital, reducing inconvenience and eliminating the risk of hospital acquired RSV disease. This is in addition to the inherent reduction in batch to batch variation of monoclonal antibody preparations and the reduction of the danger of iatrogenic infections when compared to pooled human globulin. In fact, the reduced volumes of antibody preparations required for therapy will allow, in general, treatment of patients with RSV disease by administration of antibodies intramuscularly. Aerosol therapy is another form of treatment made possible as a result of the increased specific activity of monoclonal antibodies, and is also associated with a decrease in the amount of antibodies required. This type of therapy is highly efficient due to the introduction of antibodies directly to the site of infection in the lungs. The neutralizing ability of Fab fragments of the RSV monoclonal antibodies in vivo, by aerosol application or systemic therapy, has been well demonstrated.

Neutralizing epitopes on the RSV virus are mainly confined to the major surface antigens: the F glycoprotein (viral fusion) and G glycoprotein (viral attachment). Antiserum prepared against either glycoprotein F or glycoprotein G may neutralize RSV with high efficiency (Walsh, et al., *J. Gen. Microbiol.*, 67:505, 1986). However antibodies to glycoprotein F are more frequently neutralizing for RSV. Antiserum to glycoprotein F also inhibits fusion of RSV-infected cells to neighboring uninfected cells. For therapeutic purposes, antibody preparations should neutralize a wide range of RSV isolates, including those of both antigenic subgroups. There are two antigenic subgroups of RSV, A and B, which are each present at all times in the population but which vary in proportion at any given time. Subgroups A and B are 50% related in glycoprotein F at the DNA sequence level, but appear to be more highly related in the neutralization epitope regions. In contrast, subgroups A and B are only 10% related in glycoprotein G (McIntosh and Chanock, supra). During the last several years, the efficiency of topical immunotherapy for RSV infection has been increased by two modifications of previous methodology. First, a mixture of RSV F immune monoclonal antibodies directed at the major conserved neutralization epitopes on this glycoprotein was shown effective in topical immunotherapy of RSV infection in the cotton rat. Second, delivery of RSV polyclonal antibodies directly into the lungs in a small particle aerosol (less than 2 µm) was also effective therapeutically. The use of monoclonal antibodies should decrease the amount of IgG required for therapy by at least 2 orders of magnitude. In other studies in cotton rats, parainfluenza virus type 3 (PIV3) antibodies were also shown to be therapeutic against PIV3 when administered directly into the respiratory tract. This form of topical immunotherapy has general application for respiratory viral pathogens causing disease in the cells lining the lumen of the lower respiratory tract.

Humanized mouse monoclonal antibodies (MAb), due to the contribution of the grafted mouse CDR sequences, retain a significant proportion of mouse sequence, representing 25-30% of the V-regions. There is no evidence to suggest any relationship between the mouse RSV 19 (Taylor et al., *Immunology* 52: 137-142, 1984) and published human antibody V-region CDR sequences (Winter et al., *Eur. I. Immunol.* 21:985-991, 1991) and hence repeated administration of humanized mouse MAb, as a consequence of the surface location of the CDR regions on the antibody molecule, is likely to result in a human anti-mouse MAb (HAMMA) response. This response would then preclude further therapeutic use of the humanized mouse MAb and in particular preclude any use of these humanized mouse MAb sequences for antibody gene therapy, in which case the therapy could not be withdrawn and might adversely affect the health of the patient. HAMMA responses are common in patients given conventional systemic therapy with mouse MAb, resulting in up to 50% of patients responding after the first dose and up to 95% of patients responding after the second dose. The use of pooled human gamma globulin has been universal for prophylaxis in hepatitis and for treatment in hepatitis, Junin virus induced hemorrhagic fever and RSV infection, with no side effects severe enough to preclude this form of passive immunization. Hence, by inference, the application of a human monoclonal Fab to this form of therapy should have no serious consequence such as that induced by the HAMMA response to mouse antibody or fragments thereof.

For long term prophylaxis of RSV infection in immunosuppressed patients or newborn infants who lack an intact immune system, it would be preferable to apply an immunoglobulin preparation for passive immunization which includes more than one neutralizing epitope on the RSV F glycoprotein. This is due to the mutation rate of the RSV F glycoprotein for any single neutralization site being in the range $10^{-4}$ to $10^{-5}$, the rate for two neutralization sites being thus $10^{-8}$ to $10^{-10}$, for three neutralization sites being $10^{-12}$ to $10^{-15}$ and so on. Administration of anti-RSV antibodies or fragments thereof, over a significant period of time in multiple patients or as multiple periods of treatment in a single patient, would create a significant selective pressure for the development of escape mutants. Hence, to counteract this selective pressure, the inclusion of antibodies or fragments to two or more neutralization epitopes is preferable in any preparation to be used for passive immunization. However, prior to the present invention, only one other neutralizing human monoclonal RSV antibody or fragment thereof, was known. The human Fab RSV19 of Barbas et al. (*Proc. Natl. Acad. Sci.* (USA) 89:10164-10168, 1992), included in PCT International Publication Number WO 94/06448, has an amino acid sequence completely unrelated to those of the anti-RSV antibodies of the present invention. More important, the RSV19 human Fab binds to an unrelated neutralization epitope on the RSV F glycoprotein epitope, representing the "B" epitope or antigenic site, recognized by the mouse MAb 1269 (Taylor et al., *Immunology* 52:137-142, 1984). Hence the uniqueness of the anti-RSV antibodies of the present invention and the human Fab RSV 19, in both aa sequence and epitopic site, has important implications for the design of immunotherapeutic vaccines or modalities for the treatment of RSV disease.

SUMMARY OF THE INVENTION

The present invention relates to monoclonal antibodies which bind to an epitope on the RSV F glycoprotein which include amino acid (aa) residue number 429 or which bind to an epitope affected conformationally by a single aa change at this position, and which neutralize with high efficiency antigenic subgroups A and B of respiratory syncytial virus (RSV). Also described are human immunoglobulin heavy chain and light chain V-region amino acid sequences which confer neutralization function to the paratope of these monoclonal antibodies. The monoclonal antibodies of the invention have particular utility as pharmaceuticals and reagents for the immunoprophylaxis, immunotherapy and diagnosis of RSV disease. The present invention also provides cell lines and vectors producing or encoding the monoclonal antibodies of the invention.

A major advantage of the monoclonal antibodies of the invention derives from the fact that they include human CDR3 sequences and, in some embodiments, may be entirely human monoclonal antibodies. Hence in vivo use of the fully human monoclonal antibodies of the invention for immunoprophylaxis and immunotherapy of RSV disease greatly reduces the problem of host immune response to passively administered antibodies. This problem is commonly encountered when the prior art monoclonal antibodies of xenogeneic or chimeric derivation are utilized. A second important aspect of this advantage is the potential safety of these human monoclonal antibodies for gene therapy applications, in which expression of xenogeneic or chimeric proteins containing non-human sequences cannot be terminated.

The antibodies of the invention are particularly efficacious for immunotherapy of RSV disease when administered directly to the lungs in the form of Fab fragments. Topical delivery of RSV antibodies directly into the lungs has a major advantage over parenteral administration of antibodies for therapy of RSV disease. Polyclonal antibodies delivered by the former route are approximately 80 to 160 times more effective in therapy, thereby decreasing the amount of antibody required for therapy by a factor of 80 to 160. A further reduction in the amount of antibody required for therapy, by a factor of 25 to 50, can be achieved by using monoclonal rather than polyclonal antibodies. This means that the total amount of antibody required for therapy by parenteral treatment can be reduced by a factor of 2000 to 8000 when monoclonal antibodies are administered directly into the lungs for treatment of RSV infection. The ability to utilize Fab or Fd fragments in vivo for respiratory viral infections provides significant advantages over the use of whole antibody molecules including: (1) greater tissue penetration; (2) avoidance of effector functions associated with Fc such as inflammation; and (3) rapid clearance.

The in vivo therapeutic effectiveness of Fab fragments in treating viral infection has been demonstrated for RSV and coronaviruses. This is despite the fact that Fabs are monovalent, precluding antigen cross linking, which was commonly thought to be necessary for viral neutralization; and that the Fc portion was thought to be necessary for viral clearance as a consequence of complement activation and antibody dependent cell cytotoxicity (ADCC).

In particular, the present invention provides substantially pure polypeptides comprising antibodies selectively binding to an RSV F glycoprotein epitope, wherein the antibodies include a heavy chain CDR3 region having the RSVF2-5 heavy chain CDR3 amino acid sequence of SEQ ID NO: 7. Such antibodies include fragment antibodies which are Fd, Fv and Fab fragments. The invention further provides such antibodies which include the heavy chain CDR2 region of SEQ ID NO: 5, and/or the heavy chain CDR1 region of SEQ ID NO: 3. In particularly preferred embodiments, the antibodies of the invention include the entire RSVF2-5 heavy chain Fd sequence of SEQ ID NO: 1.

In some embodiments, the antibodies of the invention are Fab fragments and further include the light chain CDR3 region of SEQ ID NO: 15, the light chain CDR2 region of SEQ ID NO: 13, and/or the light chain CDR1 region having the amino acid sequence of SEQ ID NO: 11. In particularly preferred embodiments the antibodies of the present invention include the entire RSVF2-5 light chain sequence of SEQ ID NO: 9.

Because the major antigen binding domain of antibodies is the heavy chain CDR3 region, the present invention also provides polypeptides which consist of, or consist essentially of, the heavy chain CDR3 region of the RSVF2-5 antibody disclosed as SEQ ID NO: 7.

The present invention also provides pharmaceutical preparations comprising a pharmaceutically acceptable carrier and any one or more of the antibodies described above.

In another series of embodiments, the present invention also provides isolated nucleic acids comprising nucleotide sequences encoding the antibodies described above. In particular, the present invention provides such nucleic acids in the form of vectors including regulatory sequences operably joined to said nucleotide sequences.

The present invention also provides pharmaceutical preparations comprising a pharmaceutically acceptable carrier; and any one or more of the nucleic acids described above.

In another set of embodiments, the present invention provides a method for the treatment of RSV disease comprising administering to a human or other animal subject in need of such treatment a therapeutically effective amount of the antibody and/or nucleic acid pharmaceutical compositions described above. The methods can be for prophylaxis of RSV infection or for treatment of active RSV disease.

In yet another set of embodiments, the present invention provides a method of detecting the presence of RSV in a biological sample comprising contacting such a sample with any one or more of the antibodies described above. In another set of embodiments, the invention provides a method of detecting the presence of RSV in vivo comprising contacting a subject with an effective amount of any one or more of the antibodies described above, the antibodies contained in a pharmaceutically acceptable carrier. Binding of the antibodies to RSV, then can be detected as a determination of the presence of RSV.

The invention also involves the use of the antibodies and/or nucleic acids described above in the preparation of a medicament. The medicament can be for any of the diagnostic and/or therapeutic purposes discussed herein.

Finally, the present invention provides host cells including a vector comprising a nucleic acid encoding one of the antibodies of the present invention.

DETAILED DESCRIPTION OF THE INVENTION

Definitions

As used herein, the term "antibody" means an immunoglobulin molecule or a fragment of an immunoglobulin molecule having the ability to specifically bind to a particular antigen. Antibodies are well known to those of ordinary skill in the science of immunology. As used herein, the term "antibody" means not only intact antibody molecules but also fragments of antibody molecules retaining antigen binding ability. Such fragments are also well known in the art and are regularly employed both in vitro and in vivo. In particular, as used herein, the term "antibody" means not only intact immunoglobulin molecules but also antigen binding active fragments such as the well-known active fragments $F(ab')_2$, Fab, Fv, and Fd.

As used herein, the term "RSV disease" means any disease caused, directly or indirectly, by a Respiratory Syncytial Virus (RSV) as well as diseases or conditions which predispose a patient to infection by RSV. Examples of diseases falling into the former category include pneumonia and bronchiolitis. Diseases and conditions in the latter category (i.e., those which place the patient at risk of severe RSV infection) include cystic fibrosis, congenital heart disease, cancer, age related immunosuppression and, generally, any condition that causes a state of immunosuppression or decreased function of the immune system such as post-operative organ transplantation regimens or premature birth.

As used herein with respect to polypeptides, the term "substantially pure" means that the polypeptides are essentially free of other substances with which they may be found in nature or in vivo systems to an extent practical and appropriate for their intended use. In particular, the polypeptides are sufficiently pure and are sufficiently free from other biological constituents of their hosts cells so as to be useful in, for example, generating antibodies, sequencing, or producing pharmaceutical preparations. By techniques well known in the art, substantially pure polypeptides may be produced in light of the nucleic acid and amino acid sequences disclosed herein. Because a substantially purified polypeptide of the invention may be admixed with a pharmaceutically acceptable carrier in a pharmaceutical preparation, the polypeptide may comprise only a small percentage by weight of the preparation. The polypeptide is nonetheless substantially pure in that it has been substantially separated from the substances with which it may be associated in living systems.

As used herein with respect to nucleic acids, the term "isolated" means: (I) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

As used herein, a coding sequence and regulatory sequences are said to be "operably joined" when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined gene. Regulatory sequences may also include enhancer sequences or upstream activator sequences, as desired.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a 1]1ic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

Novel Anti-RSV Monoclonal Antibodies.

The present invention derives, in part, from the isolation and characterization of a novel, fully human monoclonal antibody which selectively binds to and neutralizes RSV and which we have designated RSVF2-5. As described more fully below, this new monoclonal antibody has been shown to bind to the RSV F glycoprotein and to neutralize RSV in vivo. The paratope of the RSVF2-5 Fab fragment associated with the neutralization epitope on the RSV F glycoprotein F1 subunit is defined by the amino acid (aa) sequences of the immunoglobulin heavy and light chain V-regions depicted in Table 5 and SEQ ID NO: 1 and SEQ ID NO: 9. The nucleic acid sequences coding for these aa sequences were identified as described in Example 1, by sequencing from both the 5' and 3' ends of the Fd heavy chain fragment and light chain. These nucleic acid sequences have been deposited with the National Center for Genome Resources (accession numbers L41061 and L41062) and are disclosed herein as SEQ ID NO: 21 and SEQ ID NO: 22. However, due to the degeneracy of the DNA code, the paratope is more properly defined by the derived aa sequences depicted in Table 5, in SEQ ID NO: 1 and SEQ ID NO: 9.

The antibodies of the present invention selectively bind to an epitope on the RSV F glycoprotein which either includes amino acid (aa) residue number 429 or which is affected conformationally by a single aa change at this position. This is demonstrated by the ability of the antibodies of the present invention to neutralize RSV strains in which position 429 of the RSV F glycoprotein is occupied by an arginine residue but not an RSV strain in which this position is occupied by a serine residue (see Example 3, Table 4). A murine antibody and humanized murine antibodies specific for a similar, if not identical. RSV epitope were described in PCT International Publication Number WO 92/04381. Of particular importance, the antibodies of the present invention are specific for, and neutralize, both the A and B antigenic subgroups of the respiratory syncytial virus.

In one set of embodiments, the present invention provides the intact, fully human RSVF2-5 monoclonal antibody in isolated form and in pharmaceutical preparations. Similarly, as described below, the present invention provides isolated nucleic acids, host cells transformed with nucleic acids, and pharmaceutical preparations including isolated nucleic acids, encoding the intact, fully human RSVF2-5 monoclonal antibody. Finally, the present invention provides methods, as described more fully below, employing these antibodies and nucleic acids in the in vitro and in vivo diagnosis and therapy of RSV disease.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology,* 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

The complete amino acid sequences of the antigen-binding. Fab portion of the RSVF2-5 monoclonal antibody as well as the relevant FR and CDR regions are disclosed herein. SEQ ID NO: 1 discloses the amino acid sequence of the Fd fragment of RSVF2-5. The amino acid sequences of the heavy chain FR1, CDR1, FR2, CDR2, FR3, CDR3 and FR4 regions are disclosed as SEQ ID NO: 2 through SEQ ID NO: 8, respectively. SEQ ID NO: 9 discloses the amino acid sequence of the light chain of RSVF2-5. The amino acid sequences of the light chain FR1, CDR1, FR2, CDR2, FR3, CDR3 and FR4 regions are disclosed as SEQ ID NO: 10 through SEQ ID NO: 16, respectively.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments of the RSVF2-5 monoclonal antibody; chimeric antibodies in which the Fc and/or FR and/or CDR1 and/or CDR2 and/or light chain CDR3 regions of the RSVF2-5 antibody have been replaced by homologous human or non-human sequences; chimeric F(ab')$_2$ fragment antibodies in which the FR and/or CDR1 and/or CDR2 and/or light chain CDR3 regions of the RSVF2-5 antibody have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. Thus, those skilled in the art may alter the RSVF2-5 antibody by the construction of CDR grafted or chimeric antibodies or antibody fragments containing, all or part thereof, of the disclosed heavy and light chain V-region CDR aa sequences (Jones et al., *Nature* 321:522, 1986; Verhoeyen et al., *Science* 39:1534, 1988 and Tempest et al., *Biotechnology* 9:266, 1991), without destroying the specificity of the antibodies for the RSVF glycoprotein epitope. Such CDR grafted or chimeric antibodies or antibody fragments can be effective in prevention and treatment of RSV infection in animals (e.g. cattle) and man.

In preferred embodiments, the chimeric antibodies of the invention are fully human monoclonal antibodies including at least the heavy chain CDR3 region of the RSVF2-5 antibody. As noted above, such chimeric antibodies may be produced in which some or all of the FR regions of RSVF2-5 have been replaced by other homologous human FR regions. In addition, the Fc portions may be replaced so as to produce IgA or IgM as well as IgG antibodies bearing some or all of the CDRs of the RSVF2-5 antibody. Of particular importance is the inclusion of the RSVF2-5 heavy chain CDR3 region and, to a lesser extent, the other CDRs of RSVF2-5. Such fully human chimeric antibodies will have particular utility in that they will not evoke an immune response against the antibody itself.

It is also possible, in accordance with the present invention, to produce chimeric antibodies including non-human sequences. Thus, one may use, for example, murine, ovine, equine, bovine or other mammalian Fc or FR sequences to replace some or all of the Fc or FR regions of the RSVF2-5 antibody. Some of the CDRs may be replaced as well. Again, however, it is preferred that at least the heavy chain CDR3 region of the RSVF2-5 antibody be included in such chimeric antibodies and, to a lesser extent, it is also preferred that some or all of the other CDRs of RSVF2-5 be included. Such chimeric antibodies bearing non-human immunoglobulin sequences admixed with the CDRs of the human RSVF2-5 monoclonal antibody are not preferred for use in humans and are particularly not preferred for extended use because they may evoke an immune response against the non-human sequences. They may, of course, be used for brief periods or in immunosuppressed individuals but, again, fully human antibodies are preferred. Because, however, RSV also infects animals such as cattle, and because such antibodies may be used for brief periods or in immunosuppressed subjects, chimeric antibodies bearing non-human mammalian Fc and FR sequences but including at least the RSVF2-5 heavy chain CDR3 are contemplated as alternative embodiments of the present invention.

For inoculation or prophylactic uses, the antibodies of the present invention are preferably intact antibody molecules including the Fc region. Such intact antibodies will have longer half-lives than smaller fragment antibodies (e.g. Fab) and are more suitable for intravenous, intraperitoneal, intramuscular, intracavity, subcutaneous, or transdermal administration.

When administered topically to the lumenal lining of the lungs, as by aerosol, Fab fragments, including chimeric Fab fragments, are preferred. Fabs offer several advantages over F(ab')2 and whole immunoglobulin molecules for this therapeutic modality. First, because Fabs have only one binding site for their cognate antigen, the formation of immune complexes is precluded whereas such complexes can be generated when bivalent F(ab')$_2$, and whole immunoglobulin molecules encounter their target antigen. This is of some importance because immune complex deposition in tissues can produce adverse inflammatory reactions. Second, because Fabs lack an Fc region they cannot trigger adverse inflammatory reactions that are activated by Fc, such as activation of the complement cascade. Third, the tissue penetration of the small Fab molecule is likely to be much better than that of the larger whole antibody. Fourth, Fabs can be produced easily and inexpensively in bacteria, such as *E. coli*, whereas whole immunoglobulin antibody molecules require mammalian cells for their production in useful amounts. The latter entails transfection of immunoglobulin sequences into mammalian cells with resultant transformation. Amplification of these sequences must then be achieved by rigorous selective procedures and stable transformants must be identified and maintained. The whole immunoglobulin molecules must be produced by stably transformed, high expression mammalian cells in culture with the attendant problems of serum-containing culture medium. In contrast, production of Fabs in *E. coli* eliminates these difficulties and makes it possible to produce these antibody fragments in large fermenters which are less expensive than cell culture-derived products.

In addition to Fabs, smaller antibody fragments and epitope-binding peptides having binding specificity for the RSVF2-5 epitope of RSV are also contemplated by the present invention and can also be used to neutralize the virus. For example, single chain antibodies can be constructed according to the method of U.S. Pat. No. 4,946,778, to Ladner et al., which is incorporated herein by reference. Single chain antibodies comprise the variable regions of the light and heavy chains joined by a flexible linker moiety. Yet smaller is the antibody fragment known as the single domain antibody or Fd, which comprises an isolated VH single domain. Techniques for obtaining a single domain antibody with at least some of the binding specificity of the intact antibody from which they are derived are known in the art. For example, Ward, et al., *Nature* 341: 644-646 (1989), disclose a method of screening to identify an antibody heavy chain variable region ($V_H$ single domain antibody) with sufficient affinity for its target epitope to bind thereto in isolated form.

It is possible to determine, without undue experimentation, if an altered or chimeric antibody has the same specificity as the RSVF2-5 antibody of the invention by ascertaining whether the former blocks the latter from binding to RSV. If the monoclonal antibody being tested competes with the RSVF2-5 antibody, as shown by a decrease in binding of the RSVF2-5 antibody, then it is likely that the two monoclonal antibodies bind to the same, or a closely related, epitope. Still another way to determine whether a monoclonal antibody has the specificity of the RSVF2-5 antibody of the invention is to pre-incubate the RSVF2-5 antibody with RSV with which it is normally reactive, and then add the monoclonal antibody being tested to determine if the monoclonal antibody being tested is inhibited in its ability to bind RSV. If the monoclonal antibody being tested is inhibited then, in all likelihood, it has the same, or a functionally equivalent, epitope and specificity as the RSVF2-5 antibody of the invention. Screening of monoclonal antibodies of the invention, also can be carried out utilizing RSV and determining whether the monoclonal antibody neutralizes RSV.

By using the antibodies of the invention, it is now possible to produce anti-idiotypic antibodies which can be used to screen other monoclonal antibodies to identify whether the antibody has the same binding specificity as an antibody of the invention. In addition, such anti-idiotypic antibodies can be used for active immunization (Herlyn, et al., *Science,* 232: 100, 1986). Such anti-idiotypic antibodies can be produced using well-known hybridoma techniques (Kohler and Milstein, *Nature,* 256:495, 1975). An anti-idiotypic antibody is an antibody which recognizes unique determinants present on the monoclonal antibody produced by the cell line of interest. These determinants are located in the hypervariable region of the antibody. It is this region which binds to a given epitope and, thus, is responsible for the specificity of the antibody. An anti-idiotypic antibody can be prepared by immunizing an animal with the monoclonal antibody of interest. The immunized animal will recognize and respond to the idiotypic determinants of the immunizing antibody and produce an antibody to these idiotypic determinants. By using the anti-idiotypic antibodies of the immunized animal, which are specific for the monoclonal antibodies of the invention, it is possible to identify other clones with the same idiotype as the antibody of the hybridoma used for immunization. Idiotypic identity between monoclonal antibodies of two cell lines demonstrates that the two monoclonal antibodies are the same with respect to their recognition of the same epitopic determinant. Thus, by using anti-idiotypic antibodies, it is possible to identify other hybridomas expressing monoclonal antibodies having the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the image of the epitope bound by the first monoclonal antibody. Thus, the anti-idiotypic monoclonal antibody can be used for immunization, since the anti-idiotype monoclonal antibody binding domain effectively acts as an antigen.

Nucleic Acids Encoding Anti-RSV Antibodies

Given the disclosure herein of the amino acid sequences of the heavy chain Fd and light chain variable domains of the RSVF2-5 anti-RSV antibody, one of ordinary skill in the art is now enabled to produce nucleic acids which encode this antibody or which encode the various fragment antibodies or chimeric antibodies described above. It is contemplated that such nucleic acids will be operably joined to other nucleic acids forming a recombinant vector for cloning or for expression of the antibodies of the invention. The present invention includes any recombinant vector containing the coding sequences, or part thereof, whether for prokaryotic or eukaryotic transformation, transfection or gene therapy. Such vectors may be prepared using conventional molecular biology techniques, known to those with skill in the art, and would comprise DNA coding sequences for the RSVF2-5 immunoglobulin V-regions including framework and CDRs or parts thereof, and a suitable promoter either with (Whittle et al., *Protein Eng.* 1:499, 1987 and Burton et al., *Science* 266: 1024-1027, 1994) or without (Marasco et al., *Proc. Natl. Acad. Sci.* (USA) 90:7889, 1993 and Duan et al., *Proc. Natl.*

Acad. Sci. (USA) 91:5075-5079, 1994) a signal sequence for export or secretion. Such vectors may be transformed or transfected into prokaryotic (Huse et al., Science 246:1275, 1989, Ward et al., Nature 341: 644-646,1989; Marks et al., *J. Mol. Biol.* 222:581, 1991 and Barbas et al., *Proc. Natl. Acad. Sci.* (USA) 88:7978, 991) or eukaryotic (Whittle et al., 1987 and Burton et al., 1994) cells or used for gene therapy (Marasco et al., 1993 and Duan et al., 1994) by conventional techniques, known to those with skill in the art.

The expression vectors of the present invention include regulatory sequences operably joined to a nucleotide sequence encoding one of the antibodies of the invention. As used herein, the term "regulatory sequences" means nucleotide sequences which are necessary for or conducive to the transcription of a nucleotide sequence which encodes a desired polypeptide and/or which are necessary for or conducive to the translation of the resulting transcript into the desired polypeptide. Regulatory sequences include, but are not limited to, 5' sequences such as operators, promoters and ribosome binding sequences, and 3' sequences such as polyadenylation signals. The vectors of the invention may optionally include 5' leader or signal sequences, 5' or 3' sequences encoding fusion products to aid in protein purification, and various markers which aid in the identification or selection of transformants. The choice and design of an appropriate vector is within the ability and discretion of one of ordinary skill in the art. The subsequent purification of the antibodies may be accomplished by any of a variety of standard means known in the art.

A preferred vector for screening monoclonal antibodies, but not necessarily preferred for the mass production of the antibodies of the invention, is a recombinant DNA molecule containing a nucleotide sequence that codes for and is capable of expressing a fusion polypeptide containing, in the direction of amino- to carboxy-terminus, (1) a prokaryotic secretion signal domain, (2) a polypeptide of the invention, and, optionally, (3) a fusion protein domain. The vector includes DNA regulatory sequences for expressing the fusion polypeptide, preferably prokaryotic regulatory sequences. Such vectors can be constructed by those with skill in the art and have been described by Smith et al. (*Science* 228:1315-1317, 1985), Clackson et al. (*Nature* 352:624-628, 1991); Kang et al. (in "Methods: A Companion to Methods in Enzymology: Vol. 2", R. A. Lerner and D. R. Burton, ed. Academic Press, NY, pp 111-118, 1991); Barbas et al. (*Proc. Natl. Acad. Sci.* (USA) 88:7978-7982, 1991), Roberts et al. (*Proc. Natl. Acad. Sci.* (USA) 89:2429-2433, 1992)

A fusion polypeptide may be useful for purification of the antibodies of the invention. The fusion domain may, for example, include a poly-His tail which allows for purification on Ni+ columns or the maltose binding protein of the commercially available vector pMAL (New England BioLabs, Beverly, Mass.). A currently preferred, but by no means necessary, fusion domain is a filamentous phage membrane anchor. This domain is particularly useful for screening phage display libraries of monoclonal antibodies but may be of less utility for the mass production of antibodies The filamentous phage membrane anchor is preferably a domain of the cpIII or cpVIII coat protein capable of associating with the matrix of a filamentous phage particle, thereby incorporating the fusion polypeptide onto the phage surface, to enable solid phase binding to specific antigens or epitopes and thereby allow enrichment and selection of the specific antibodies or fragments encoded by the phagemid vector.

The secretion signal is a leader peptide domain of a protein that targets the protein membrane of the host cell, such as the periplasmic membrane of gram negative bacteria. A preferred secretion signal for *E. coli* is a pelB secretion signal. The predicted amino acid residue sequences of the secretion signal domain from two pelB gene producing variants from *Erwinia carotova* are described in Lei, et al. *Nature* 381:543-546, 1988). The leader sequence of the pelB protein has previously been used as a secretion signal for fusion proteins (Better, et al., *Science* 240:1041-1043, 1988; Sastry, et al., *Proc. Natl. Acad. Sci.* (USA) 86:5728-5732, 1989; and Mullinax, et al., *Proc. Natl. Acad. Sci.* (USA) 87:8095-8099, 1990). Amino acid residue sequences for other secretion signal polypeptide domains from *E. coli* useful in this invention can be found in Oliver, In Neidhard, F. C. (ed.), *Escherichia coli and Salmonella Typhimurium*, American Society for Microbiology, Washington, D.C., 1:56-69 (1987).

To achieve high levels of gene expression in *E. coli*, it is necessary to use not only strong promoters to generate large quantities of mRNA, but also ribosome binding sites to ensure that the mRNA is efficiently translated. In *E. coli*, the ribosome binding site includes an initiation codon (AUG) and a sequence 3-9 nucleotides long located 3-11 nucleotides upstream from the initiation codon (Shine, et al., *Nature* 254:34, 1975). The sequence, AGGAGGU, which is called the ShineDalgarno (SD) sequence, is complementary to the 3' end of *E. coli* 16S rRNA. Binding of the ribosome to mRNA and the sequence at the 3' end of the mRNA can be affected by several factors:

(i) The degree of complementarity between the SD sequence and 3' end of the 16S rRNA.

(ii) The spacing and possibly the DNA sequence lying between the SD sequence and the AUG (Roberts, et al., *Proc. Natl. Acad. Sci.* (USA) 76:760., 1979a: Roberts, et al., *Proc. Natl. Acad. Sci.* (USA) 76:5596, 1979b; Guarente, et al., *Science* 209: 1428, 1980; and Guarente, et al., *Cell* 20:543, 1980). Optimization is achieved by measuring the level of expression of genes in plasmids in which this spacing is systematically altered. Comparison of different mRNAs shows that there are statistically preferred sequences from positions −20 to +13 (where the A of the AUG is position 0) (Gold, et al., *Annu. Rev. Microbiol.* 35:365, 1981). Leader sequences have been shown to influence translation dramatically (Roberts, et al., 1979a, b supra).

(iii) The nucleotide sequence following the AUG, which affects ribosome binding (Taniguchi, et al.,*J. Mol. Biol.*, 118:533, 1978).

The 3' regulatory sequences define at least one termination (stop) codon in frame with and operably joined to the heterologous fusion polypeptide.

In preferred embodiments with a prokaryotic expression host, the vector utilized includes a prokaryotic origin of replication or replicon, i.e., a DNA sequence having the ability to direct autonomous replication and maintenance of the recombinant DNA molecule extrachromosomally in a prokaryotic host cell, such as a bacterial host cell, transformed therewith. Such origins of replication are well known in the art. Preferred origins of replication are those that are efficient in the host organism. A preferred host cell is *E. coli*. For use of a vector in *E. coli*, a preferred origin of replication is ColE I found in pBR322 and a variety of other common plasmids. Also preferred is the p15A origin of replication found on pACYC and its derivatives. The ColEI and p15A replicons have been extensively utilized in molecular biology, are available on a variety of plasmids and are described by Sambrook. et al., *Molecular Cloning: A Laboratory Manual,* 2nd edition, Cold Spring Harbor Laboratory Press, 1989).

In addition, those embodiments that include a prokaryotic replicon preferably also include a gene whose expression confers a selective advantage, such as drug resistance, to a bacterial host transformed therewith. Typical bacterial drug resistance genes are those that confer resistance to ampicillin, tetracycline, neomycin/kanamycin or chloramphenicol. Vectors typically also contain convenient restriction sites for insertion of translatable DNA sequences. Exemplary vectors are the plasmids pUC18 and pUC19 and derived vectors such as pcDNAII available from Invitrogen, (San Diego, Calif.).

When the antibody of the invention include both heavy chain and light chain sequences, these sequences may be encoded on separate vectors or, more conveniently, may be expressed by a single vector. The heavy and light chain may, after translation or after secretion, form the heterodimeric structure of natural antibody molecules. Such a heterodimeric antibody may or may not be stabilized by disulfide bonds between the heavy and light chains.

A vector for expression of heterodimeric antibodies, such as the intact antibodies of the invention or the F(ab')$_2$, Fab or Fv fragment antibodies of the invention, is a recombinant DNA molecule adapted for receiving and expressing translatable first and second DNA sequences. That is, a DNA expression vector for expressing a heterodimeric antibody provides a system for independently cloning (inserting) the two translatable DNA sequences into two separate cassettes present in the vector, to form two separate cistrons for expressing the first and second polypeptides of a heterodimeric antibody. The DNA expression vector for expressing two cistrons is referred to as a dicistronic expression vector.

Preferably, the vector comprises a first cassette that includes upstream and downstream DNA regulatory sequences operably joined via a sequence of nucleotides adapted for directional ligation to an insert DNA. The upstream translatable sequence preferably encodes the secretion signal as described above. The cassette includes DNA regulatory sequences for expressing the first antibody polypeptide that is produced when an insert translatable DNA sequence (insert DNA) is directionally inserted into the cassette via the sequence of nucleotides adapted for directional ligation.

The dicistronic expression vector also contains a second cassette for expressing the second antibody polypeptide. The second cassette includes a second translatable DNA sequence that preferably encodes a secretion signal, as described above, operably joined at its 3' terminus via a sequence of nucleotides adapted for directional ligation to a downstream DNA sequence of the vector that typically defines at least one stop codon in the reading frame of the cassette. The second translatable DNA sequence is operably joined at its 5' terminus to DNA regulatory sequences forming the 5' elements. The second cassette is capable, upon insertion of a translatable DNA sequence (insert DNA), of expressing the second fusion polypeptide comprising a secretion signal with a polypeptide coded by the insert DNA.

The antibodies of the present invention may also, of course, be produced by eukaryotic cells such as CHO cells, human hybridomas, immortalized B-lymphoblastoid cells, and the like. In this case, a vector is constructed in which eukaryotic regulatory sequences are operably joined to the nucleotide sequences encoding the antibody polypeptide or polypeptides. The design and selection of an appropriate eukaryotic vector is within the ability and discretion of one of ordinary skill in the art. The subsequent purification of the antibodies may be accomplished by any of a variety of standard means known in the art.

In another embodiment, the present invention provides host cells, both prokaryotic and eukaryotic, transformed or transfected with, and therefore including, the vectors of the present invention.

Diagnostic and Pharmaceutical Anti-RSV Antibody Preparations

The invention also relates to a method for preparing diagnostic or pharmaceutical compositions comprising the monoclonal antibodies of the invention or polynucleotide sequences encoding the antibodies of the invention or part thereof, the pharmaceutical compositions being used for immunotherapy of RSV disease. The pharmaceutical preparation includes a pharmaceutically acceptable carrier. Such carriers, as used herein, means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

A preferred embodiment of the invention relates to monoclonal antibodies whose heavy chains comprise in CDR3 the polypeptide PVANIDY (SEQ ID NO: 7), and/or whose light chains comprise in CDR3 the polypeptide QSYDSENPWV (SEQ ID NO: 15) and conservative variations of these peptides. Also encompassed by the present invention are certain amino acid sequences that bind to epitopic sequences in glycoprotein F of RSV which include aa residue number 429 or which are conformationally affected by a single change at aa residue number 429 from arginine to serine, and which confer neutralization of RSV when bound thereto. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagines, and the like. The term "conservative variation" also includes the use of a substituted amino acid in place of an unsubstituted parent amino acid provided that antibodies having the substituted polypeptide also neutralize RSV. Analogously, another preferred embodiment of the invention relates to polynucleotides which encode the above noted heavy chain polypeptide and to polynucleotide sequences which are complementary to these polynucleotide sequences. Complementary polynucleotide sequences include those sequences which hybridize to the polynucleotide sequences of the invention under stringent hybridization conditions.

The anti-RSV antibodies of the invention may be labeled by a variety of means for use in diagnostic and/or pharmaceutical applications. There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibodies of the invention, or will be able to ascertain such, using routine experimentation. Furthermore, the binding of these labels to the monoclonal antibodies of the invention can be done using standard techniques common to those of ordinary skill in the art.

Another labeling technique which may result in greater sensitivity consists of coupling the antibodies to low molecular weight haptens. These haptens can then be specifically altered by means of a second reaction. For example, it is common to use haptens such as biotin, which reacts with avidin, or dinitrophenol, pyridoxal, or fluorescein, which can react with specific anti-hapten antibodies.

The materials for use in the assay of the invention are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise a human monoclonal antibody of the invention which is, or can be, detectably labeled. The kit may also have containers containing buffer(s) and/or a container comprising a reporter-means, such as a biotin-binding protein, such as avidin or streptavidin, bound to a reporter molecule, such as an enzymatic or fluorescent label.

In Vitro Detection and Diagnostics

The monoclonal antibodies of the invention are suited for in vitro use, for example, in immunoassays in which they can be utilized in liquid phase or bound to a solid phase carrier. In addition, the monoclonal antibodies in these immunoassays can be detectably labeled in various ways. Examples of types of immunoassays which can utilize the monoclonal antibodies of the invention are competitive and non-competitive immunoassays in either a direct or indirect format. Examples of such immunoassays are the radioimmunoassay (RIA) and the sandwich (immunometric) assay. Detection of antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The monoclonal antibodies of the invention can be bound to many different carriers and used to detect the presence of RSV. Examples of well-known carriers include glass, polystyrene, polypropylene, polyethylene, dextran, nylon, amylase, natural and modified cellulose, polyacrylamide, agarose and magnetite. The nature of the carrier can be either soluble or insoluble for purposes of the invention. Those skilled in the art will know of other suitable carriers for binding monoclonal antibodies, or will be able to ascertain such, using routine experimentation.

For purposes of the invention, RSV may be detected by the monoclonal antibodies of the invention when present in biological fluids and tissues. Any sample containing a detectable amount of RSV can be used. A sample can be a liquid such as urine, saliva, cerebrospinal fluid, blood, serum or the like; a solid or semi-solid such as tissues, feces, or the like; or, alternatively, a solid tissue such as those commonly used in histological diagnosis.

In Vivo Detection of RSV

In using the monoclonal antibodies of the invention for the in vivo detection of antigen, the detectably labeled monoclonal antibody is given in a dose which is diagnostically effective. The term "diagnostically effective" means that the amount of detectably labeled human monoclonal antibody is administered in sufficient quantity to enable detection of the site having the RSV antigen for which the monoclonal antibodies are specific.

The concentration of detectably labeled monoclonal antibody which is administered should be sufficient such that the binding to RSV is detectable compared to the background. Further, it is desirable that the detectably labeled monoclonal antibody be rapidly cleared from the circulatory system in order to give the best target-to-background signal ratio.

As a rule, the dosage of detectably labeled human monoclonal antibody for in vivo diagnosis will vary depending on such factors as age, sex, and extent of disease of the individual. The dosage of monoclonal antibody can vary from about 0.01 mg/kg to about 500 mg/kg, preferably 0.1 mg/kg to about 200 mg/kg, most preferably about 0.1 mg/kg to about 10 mg/kg. Such dosages may vary, for example, depending on whether multiple injections are given, on the tissue being assayed, and other factors known to those of skill in the art.

For in vivo diagnostic imaging, the type of detection instrument available is a major factor in selecting an appropriate radioisotope. The radioisotope chosen must have a type of decay which is detectable for the given type of instrument. Still another important factor in selecting a radioisotope for in vivo diagnosis is that the half-life of the radioisotope be long enough such that it is still detectable at the time of maximum uptake by the target, but short enough such that deleterious radiation with respect to the host is acceptable. Ideally, a radioisotope used for in vivo imaging will lack a particle emission but produce a large number of photons in the 140-250 keV range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions are the bifunctional chelating agents such as diethylenetriaminepentacetic acid (DTPA) and ethylenediaminetetra-acetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr and $^{56}$Fe.

The human monoclonal antibody of the invention can be used in vitro and in vivo to monitor the course of RSV disease therapy. Thus, for example, by measuring the increase or decrease in the number of cells infected with RSV or changes in the concentration of RSV present in the body or in various body fluids, it would be possible to determine whether a particular therapeutic regimen aimed at ameliorating the RSV disease is effective.

Prophylaxis and Therapy of RSV Disease

The monoclonal antibodies can also be used immunotherapeutically for RSV disease in both humans and other animals. The term, "immunotherapeutically" or "immunotherapy" as used herein in conjunction with the monoclonal antibodies of the invention denotes both prophylactic as well as therapeutic administration and both passive immunization with substantially purified polypeptide products, as well as gene therapy by transfer of polynucleotide sequences encoding the product or part thereof. Thus, the monoclonal antibodies can be administered to high-risk subjects in order to lessen the likelihood and/or severity of RSV disease or administered to subjects already evidencing active RSV infection. In the present invention, Fab fragments also neutralize RSV both in vitro and in vivo and therefore may be used therapeutically to treat RSV infection in vivo. As explained above, Fab fragments are preferred for topical administration to the lining of the lung but intact antibodies molecules are otherwise preferred.

As used herein, a "therapeutically effective amount" of the monoclonal antibodies of the invention is a dosage large enough to produce the desired effect in which the symptoms of the RSV disease are ameliorated or the likelihood of infection is decreased. A therapeutically effective amount is not, however, a dosage so large as to cause adverse side effects, such as hyperviscosity syndromes, pulmonary edema, congestive heart failure, and the like. Generally, a therapeutically effective amount may vary with the subject's age, condition, and sex, as well as the extent of the disease in the subject and can be determined by one of skill in the art. The dosage may be adjusted by the individual physician or veterinarian in the event of any complication. A therapeutically effective amount may vary from about 0.01 mg/kg to about 500 mg/kg, preferably from about 0.1 mg/kg to about 200 mg/kg, most preferably from about 0.2 mg/kg to about 20 mg/kg, in one or more dose administrations daily, for one or several days. Preferred is administration of the antibody for 2 to 5 or more consecutive days in order to avoid "rebound" of virus replication from occurring.

The monoclonal antibodies of the invention can be administered by injection or by gradual infusion over time. The administration of the monoclonal antibodies of the invention may, for example, be intravenous, intraperitoneal, intramuscular, intracavity, subcutaneous, or transdermal. When used therapeutically, a preferred route of administration of the monoclonal antibodies of the invention is by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences*, 18th edition, 1990, pp 1694-1712; incorporated by reference). Those of skill in the art can readily determine the various parameters and conditions for producing antibody aerosols without resort to undue experimentation.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Example 1

Isolation of RSVF2-5 Monoclonal Antibody Fab Fragment

PCR amplification of Fab and library construction. Peripheral blood lymphocytes were purified from 50 ml of whole heparinized blood of an HIV-1-infected donor, by single step density gradient using Histopaque-1077 (Sigma Chemical Co., St. Louis, Mo.) and washed once in Dulbecco's phosphate-buffered saline (PBS). Total RNA (30 mg) was purified from peripheral blood lymphocytes using a rapid single step guanidiniun isothiocyanate/phenol chloroform-based RNA isolation technique (Stratagene, La Jolla, Calif.), and cDNA was generated by reverse transcriptase (RT) using Superscript RNlase H (Gibco-BRL, Grand Island, N.Y.). PCR amplification of the $IgG_1$ Fd heavy chain fragments and light chains was performed for 35 cycles of 94° C.×1 min, 54° C.×1 min, 72° C.×3 min. This was followed by a single incubation at 72° C. for 10 min. 5' primers for the individual H and light chain V region gene families, and 3' constant region primers for $IgG_1$ k or 1 as previously described (Kang et al., in "Methods, A Companion to Methods in Enzymology: Vol. 2", R. A. Lerner and D. R. Burton, ed. Academic Press, NY, pp 111-118, 1991), were obtained from Operon (Alameda, Calif.). Primers contained restriction enzyme sites to allow the sequential ligation of Fd and light chain libraries into the phage display vector. Fd fragment DNA, of approximately 699 base pairs, was amplified with sites for the restriction enzymes, Xho I at the 5' end of the $V_H$ domain, and Spe I at the 3' end of the $C_{H1}$ domain, for ligation with DNA encoding the cap protein, or gene III product. Light chain DNA, of approximately 63.9 base pairs, was amplified with sites for the restriction enzymes, Sac I at the 5' end of the $V_L$ domain, and Xba I at the 3' end of the $C_L$ domain. The vector, pAbClone, was constructed from pcDNAII (Invitrogen, San Diego, Calif.) and pET20b (Novagen, Madison, Wis.) (pelB leaders), to contain DNA encoding the cap protein of the M13 filamentous phage, derived from M13 mp 18 (Stratagene, La Jolla, Calif.), with a restriction site for Spe I at the 5' end for ligation to the 3' end of DNA encoding the Fd fragment, essentially as described by Barbas et al. (*Proc. Natl. Acad. Sci.* (USA) 88:7978-7982, 1991). Infection of phagemid-bearing *E. coli* with VCSM13 helper phage (Stratagene) allowed production of a packaged phage library, with phage simultaneously expressing Fab molecules on the phage head and carrying DNA encoding the Fab molecules within the phage body.

Cloning and expression of Fab molecules. From a packaged phagemid library of $10^7$ clones, Fab binding to RSV Long strain (ATCC VR-26) proteins (abV Immune Response, Derry, N.H.) were enriched by 4 rounds of panning. RSV proteins were bound to microtiter 96 well plates (Costar, Cambridge, Mass.) at 1 mg/well in 25 ml 0.1 M NaHCO, overnight at 4° C., as previously described (Burton D. R., et al., *Proc. Natl. Acad. Sci.* (USA) 88:10134-10137, 1991). Amplification of the eluted phage between each round was performed by infection of *E. coli* XL1-Blue cells (Stratagene, La Jolla, Calif.) and packaging with VCSM13 helper phage (Stratagene, La Jolla, Calif.). Panning resulted in a 100-fold increase in the relative yield of eluted phage when compared to the second panning. DNA encoding the phage cap protein was then excised by digestion with NheI and SpeI, and the compatible ends of the vector relegated to allow production of soluble Fab molecules. Clones producing soluble Fab binding to RSV proteins were then identified by ELISA, using alkaline phosphatase conjugated goat anti-human Ig $F(ab)_2$ (Pierce, Rockford, Ill.).

Production and purification of Fab. For screening of soluble Fab producing clones, 10 ml overnight cultures in super broth (24)/50 J-µg Carbenicillin/ml (SB/Carb) were induced with 1 mM isopropyl-(beta)-D-thiogalactopyranoside (IPTG). The next morning cultures were centrifuged (4000 g for 10 min) and cell pellets were freeze/thawed three times in PBS/200 mM PMSF/0.01% $NaN_3$ (PBS/PMSF/Azide). Lysates were centrifuged (100,000 g for 5 min) and 50 µl volumes of supernatants were used in place of serum dilutions, as above, for ELISA testing. Purified Fab were produced from cell pellets of 1 liter cultures in SB/Carb, as described above. Pellets were freeze/thawed, as above, in 25 ml PBS/PMSF/Azide and centrifuged at 14,000 g for 40 min, filtered through a 0.22 mm filter and applied to a 10 ml Sepharose-4B (Pharmacia Biotech Inc., Piscataway, N.J.)/ goat anti-human F(ab')$_2$ (Pierce, Rockford, Ill.) affinity column equilibrated with PBS. After washing with 700 ml of PBS, the Fab were eluted in 50 ml of 0.2M glycine (pH 2.5), neutralized by addition of $\frac{1}{10}$ of a volume of 1M Tris (pH 9.0) and concentrated to 1 ml in a Centriprep 30 concentrator (Amicon, Beverly, Mass.). Purified, concentrated Fab were analyzed on Coomassie Blue-stained SDS-PAGE gels, run under reducing conditions, at between 1-10 µg per lane, and were greater than 95% pure in all cases.

Isolation and characterization of human Fab binding to RSV proteins. After 4 rounds of panning the library of $10^7$ clones with RSV proteins (Table 1), eight clones were isolated, which were producing soluble human Fab binding to RSV proteins. RSV protein-binding Fab were purified from the periplasmic extracts of lysed cell pellets from 1 liter cultures of XL 1-Blue, by affinity chromatography. The approximate binding constants were determined for these clones by ELISA using the purified Fab. Only one of these Fab clones, designated RSVF2-5, was specific for RSV proteins and did not react with BSA or other viral proteins. The protein expression level for the RSVF2-5 Fab varied from 500-700 mg purified protein/1 of culture. DNA sequences were determined for the Fd and light chain to allow cloning into vectors for genetic therapy (presented as SEQ ID NO: 21 and SEQ ID NO: 22) and the translated amino acid sequences are presented in Table 5 and as SEQ ID NO: 1 and SEQ ID NO: 9. Analysis of DNA insert size, molecular weights of purified expressed proteins on SDS-PAGE gels and translated DNA sequences revealed RSVF2-5 to consist of an Fd fragment and light chain (Fab fragment). Alignment of DNA sequences with the Genbank database identified the Fd fragment as belonging to the VH$_3$ gene family and the light chain to be a lambda chain of the V$_{L6}$ gene family. (Table 5). A predominance of lambda light chains in the original library (1:k DNA ratio was ~9:1) was the result of constraints imposed by the original yield of total RNA and a limited yield of k chain DNA from PCR amplification.

Fab binding constant determinations. RSV proteins were bound to ELISA plates at 0.1 mg/ml and blocked with 3% BSA/PBS, as above. Serial two-fold dilutions of purified human Fab in 1% BSA/PBS were added to wells (50 µl/well), incubated and washed, as for ELISA titrations above. Goat anti-human F(ab')$_2$ alkaline phosphatase conjugate (Pierce, Rockford, Ill.) and p-nitrophenyl phosphate solution were then added sequentially with washing between, as described above. The binding constants were determined as the Fab concentration (g/l) at 50% binding divided by the approximate molecular weight of the Fab ($5\times10^4$). Binding constant determinations were performed at least twice, on two separate batches of purified Fab.

The approximate binding constant for the human anti-RSV protein Fab RSVF2-5 was determined to be $8.7\times10^9$ M from ELISA titration of purified Fab.

DNA sequencing. Double stranded plasmid DNA was purified by Qiagen plasmid maxiprep kit (Qiagen, Chatsworth, Calif.). Sequencing was then performed on an automated 373A DNA sequencer (Applied Biosystems, Inc. (ABI), Foster City, Calif.), using a Taq fluorescent dideoxy terminator cycle sequencing kit (ABI). Both 5' vector flanking sequences specific to Fd (SEQ ID NO: 17, T3,5'-ATT AAC CCT CAC TAA AG-3') or light chain (SEQ ID NO: 18, KEF, 5'-GAA TTC TAA ACT AGC TAG TCG-3') leaders and 3' primers (SEQ ID NO: 19, SeqGz 5'-GAA GTA GTC CTT GAC CAG-3') for the C$_{H1}$ or (SEQ ID NO: 20, SeqLb 5'-GAA GTC ACT TAT GAG ACA CAC-3') for the C$_L$ domains, respectively, were employed. Derived sequences for heavy chain Fd fragments and light chains were aligned using MacVector and the Genbank database (International Biotechnologies Inc., New Haven, Conn.).

RSV Fab F2-5 specifically binds to RSV F glycoprotein. The specificity of RSVF2-5 for the RSV F glycoprotein was demonstrated by ELISA binding using purified RSV F or G glycoproteins, prepared as previously described (Walsh, et al. *J. Gen. Virol.* 65:761-767, 1984 and Walsh, et al. *J. Gen. Virol.* 66:409-415, 1985). A 1 µg/ml purified preparation of RSVF2-5 exhibited a titer of >1:16,384, while a similarly prepared suspension of a hepatitis B Fab (also 1 µg/ml) had a 1:2 titer in the same test. This preparation of Fab RSVF2-5 did not bind purified G glycoprotein, as evidenced by an ELISA titer of <1:2, while an RS µg/ml-positive adult control serum exhibited a titer of 1:4,096 in the same test.

Virus neutralization assay. Neutralization of RSV virus isolates, representing 10 isolates each from antigenic subgroups A and B, isolated over a period of 31 years from several national and international centers, was tested by a plaque reduction neutralization assay (Coates, et al., *J. Epid.,* 83:299, (1966), using Vero cell monolayer cultures. The titer of neutralizing antibody was expressed as the highest dilution of affinity purified Fab which reduced the plaque number by 60%. Results of neutralization testing of the affinity purified RSVF2-5 Fab, against these RSV isolates, are shown in Table 2. Efficient neutralization of these RSV isolates was observed between 0.2 to 3.0 µg/ml for all of the various isolates from subgroups A and B. Hence, RSVF2-5 has broad reactivity and is highly efficient in neutralizing activity, against the two antigenic subgroups of RSV. These data also indicate that the temporal stability of the neutralization epitope, identified by the human Fab RSVF2-5 is very high, being stable over a 31 year period. Titration of the same purified Fab preparation used for the subgroup testing, with the strain RSV A2, in the same in vitro test, indicated a 60% plaque reduction neutralizing titer of 1:803,471 and hence a specific activity of 0.005 µg/ml. Crude *E. coli* lysates were not tested in this assay, due to the non-specific results frequently obtained with this type of crude Fab preparation.

Example 2

The Therapeutic Efficacy of Human Monoclonal Fab RSVF2-5 in Treating RSV Infected Mice Clearance of RSV from the lungs of infected mice by purified RSVF2-5 Fab Groups of six mice were infected intranasally (i.n.) with $10^7$ pfu of RSV strain A2, in 100 µl of sterile PBS, under light methoxyflurane anesthesia, on day 0. Four days post infection, representing the height of the infection, different groups were treated with the indicated dose (Table 3) of affinity purified Fab in 100 µl of sterile PBS, instilled intranasally under the same conditions of anesthesia as for inoculation with virus. The ELISA titer of this purified Fab preparation, at a concentration of 3.6 mg/ml, was 1/60,000, the neutralization titer was 1/803,471 (Example I) and the purity was greater than 99%. Control mice were treated with PBS or with a human monoclonal Fab (HBVc41) isolated from the same combinatorial Fab library, which binds to hepatitis B virus (HBV) core antigen (Table 3). Lung tissue homogenates and nasal turbinates were prepared for virus quantitation on day 5

(18 hours post Fab treatment) (Murphy et al., Vaccine 8:497-502, 1990 and Prince et al., Am. J. Path. 93:771-792, 1978) and stored frozen until they were titered for RSV on Vero cell monolayers by plaque reduction assay (Coates, et al., J. Epid. 83:299, 1966). Plaques were detected by immunoperoxidase labeling as described by Murphy et al. (1990).

The human anti-RSV Fab RSVF2-5 was highly effective in clearing an established RSV infection from the lungs of mice (Table 3). Detectable virus was evident in the lungs of only 1 out of 6 mice treated with 4.0 mg/kg of body weight with a mean reduction of more than 3 $\log_{10}$pfu compared to that produced by treatment with the HBV core antigen Fab (HBVc41) or PBS.

Example 3

Identification of the RSVF2-5 Binding Epitope

The following example demonstrates that the human Fab RSVF2-5, which neutralizes RSV in vitro and cures mice of lung infection with RSV, identifies an epitope (linear or conformational) which includes the F glycoprotein amino acid (aa) residue number 429 or which is contormationally affected by this residue.

Neutralization of escape mutants of the RSV strain A2. Monoclonal antibody RSV escape mutants (MARM) were tested for in vitro neutralization by human monoclonal Fab RSVF2-5, using the plaque reduction assay described in Example I (Coates, et al., J. Epid. 83:299, 1966), on Vero cell monolayers. The titer of neutralizing antibody was expressed as the highest dilution of affinity purified Fab which reduced the plaque number by 60%. Results of neutralization testing of the purified RSVF2-5 Fab, against these RSV are expressed in Table 4. Affinity purified anti-RSV Fab RSVF2-5 does not neutralize the RSV MARM v324 of Dr. G. Taylor, generated using the mouse monoclonal antibody (MAb) RSV19 (Taylor et al., Immunology 52: 137-142, 1984). In contrast, RSVF2-5 Fab neutralized all other escape mutants and the wild type RSV strain A2 with neutralizing titers in the same range as that for the subgroup A and B RSV isolates tested in Example 1 (Table 2). The MARM v324 escape mutant of RSV possesses a single aa substitution (arginine to serine) at residue 429 on the F1 subunit of the RSV F glycoprotein. However the aa sequences of the RSVF2-5 human Fab $V_H$- and $V_L$-regions (Table 5) are unique and unrelated to those of the RSV19 MAb or the humanized form of this mouse antibody (see, e.g., PCT International Publication Number WO92/04381).

Hence the present invention recognizes a neutralization epitope on the RSV F glycoprotein F 1 subunit which either includes arginine residue 429 or which is remote from this residue but is affected conformationally by a substitution at that position. The associated paratope of the RSVF25 human Fab defined by the CDR-regions, in particular CDR3 of the of the $V_H$- and $V_L$-regions is suitable for the preparation of protective and therapeutic agents which neutralize RSV, in particular, for the preparation of monoclonal antibodies against the associated epitope on the RSV F glycoprotein. Knowledge of this paratope enables one of skill in the art to produce synthetic peptides or anti-idiotypic antibodies which may also be suitable as vaccines against RSV. The epitope including, or conformationally affected by, substitution at residue 429 on the RSV F glycoprotein F1 subunit, identified by the RSVF2-5 human Fab, is a suitable target for the screening of other neutralization epitopes and the production of monoclonal antibodies useful for the therapy and prophylaxis of RSV infections in humans.

RSVF2-5 was deposited at the American Type Culture Collection, 10801 University Blvd., Manassas, Va. 20110-2209 under ATCC Designation 69909.

The foregoing written specification is to be considered to be sufficient to enable one skilled in the art to practice the invention. The present invention is not to be limited in scope by the cell line deposited, since the deposited embodiment is intended as a single illustration of one aspect of the invention and any cell lines that are functionally equivalent are within the scope of the invention. Similarly, the nucleotide sequences and particular antibodies disclosed herein are not to be construed as limiting of the invention as they are intended merely as illustrative of particular embodiments of the invention as enabled herein. Therefore, any sequences or antibodies that are functionally equivalent of those described herein are within the spirit and scope of the claims appended hereto. Indeed, various modifications of the invention in addition to those shown and described herein will become apparent to those skilled in the art from the foregoing description and fall within the scope of the appended claims.

TABLE 1

ENRICHMENT OF PHAGE FROM PANNING OF CARU LIBRARY WITH RSV PROTEINS

| Pan round | Applied phage* | Eluted phage* | Relative yield |
|---|---|---|---|
| 1 | $2.4 \times 10^{12}$ | $3.3 \times 10^7$ | $1.2 \times 10^{-5}$ |
| 2 | $1.1 \times 10^{13}$ | $9.1 \times 10^6$ | $8.0 \times 10^{-7}$ |
| 3 | $1.4 \times 10^{12}$ | $7.1 \times 10^7$ | $4.9 \times 10^{-5}$ |
| 4 | $3.0 \times 10^{11}$ | $2.6 \times 10^7$ | $8.5 \times 10^{-5}$ |

*Total number of cfu in 200 ul of PBS/1% BSA

TABLE 2

NEUTRALIZATION OF RSV STRAINS FROM ANTIGENIC SUBGROUPS A AND B, BY HUMAN MONOCLONAL Fab RSVF-2-5

| RSV Virus Isolates# | Specific neutralization activity (µg/ml)* |
|---|---|
| Subgroup A | |
| SW/669/'59 | 3.0 |
| Wash/11657/'60 | 1.6 |
| Wash/Bern/'65 | 0.6 |
| SL/863/'84 | 0.2 |
| SL/10849/'84 | 0.9 |
| SL/10865/'84 | 0.4 |
| OK/9970/'85 | 1.4 |
| Bir/6190/'89 | 2.4 |
| New/RSS-2/'76 | 1.9 |
| Bir/1734/'89 | 1.1 |
| Subgroup B | |
| WV/474R/'90 | 0.9 |
| WV/1293/'75 | 1.0 |
| WV/4843/'80 | 0.5 |
| Wash/18537/'62 | 0.5 |
| WV/14617/'85 | 2.6 |
| WV/17154/'85 | 2.1 |
| WV/20323/'87 | 0.8 |
| WV/285R/'90 | 0.6 |
| WV/401R/'90 | 0.7 |
| WV/2B/'87 | 0.3 |

*Quantity of purified Fab required, for preincubation with virus, to effect a reduction of 60% in RSV induced plaques, produced in Vero cell monolayers
Abbreviations: Bir (Birmingham), New (Newcastle), OK (Oklahoma), SL (St. Louis), SW (Sweden), Wash (Washington), Wash/Bern (Washington/Bern) and WV (West Virginia). (West Virginia strains provided by M. A. Mufson, M.D.).

TABLE 3

THERAPEUTIC EFFECT OF PURIFIED RSVF2-5 HUMAN ANTI-RSV Fab IN RSV INFECTED MICE

| Treatment | Dose (mg Fab/kg body weight) | RSV titer in tissue homogenate* (mean $\log_{10}$ pfu/g tissue) Nasal turbinates | Lungs |
|---|---|---|---|
| Fab RSVF2-5 | 4.0 | 3.2 | 1.9# |
| | 1.0 | 3.8 | 3.3 |
| | 0.25 | 4.4 | 4.3 |
| | 0.0625 | 4.2 | 4.0 |
| | 0.0156 | 5.0 | 4.9 |
| | 0.0039 | 4.9 | 5.2 |
| HBVc41 Fab | 4.0 | 4.7 | 5.3 |
| | 1.0 | 4.7 | 5.3 |
| PBS | n.a | 4.5 | 5.2 |

*Titer of virus recovered from tissue homogenates 4 days post infection with RSV and 18 hours post treatment with affinity purified Fab or PBS.
Virus recovered from 1 of 6 animals at 1.7 $\log_{10}$ pfu/g detectable. Mean calculated using 1.7 for the 5 animals without detectable virus.

TABLE 4

NEUTRALIZING ABILITY OF RSVF2-5 FOR MONOCLONAL ANTIBODY ESCAPE MUTANTS OF RSV

| RSV MARM* | Dose for 60% plaque reduction (µg/ml) | Antigenic site | Amino acid substituted# |
|---|---|---|---|
| v1237 | <0.3 | A | 276 |
| v1214 | 0.1 | A | 276 |
| v1129 | 0.5 | A | 275 |
| vN151 | 0.4 | A | 272 |
| v1200 | 0.3 | A | 272 |
| v1153 | 0.9 | A | 262 |
| v1269 | <0.3 | B | 389 |
| v1308F | 1.0 | C | 241/421 |
| v1302A/1 | 1.4 | C | 241/421 |
| v1302A/6 | <0.3 | C | 241/421 |
| v324† | >18 | other | 429 |
| A2 w.t.** | 0.1 | na | na |

*Monoclonal antibody RSV escape mutants (MARM) generated from the RSV strain A2 by Dr. Geraldine Taylor.
Amino acid (aa) substitutions on the RSV F glycoprotein responsible for the resistance to neutralization.
†v324 is a MARM resistant to mouse MAb RSV19 of Geraldine Taylor, the humanized form of which is the subject of international patent application number WO92/04381. The MARM possesses a single aa change at position 429 (F1 subunit).
**Wild type RSV strain A2.

TABLE 5

V-REGION AMINO SEQUENCES OF RSVF2-5 Fd AND LIGHT CHAIN

| Region | Heavy Chain VH3 Sequence | Light Chain VL6 Sequence |
|---|---|---|
| FR1 | LEESGGDLVQ PGRSLRLSCS TSGFSFG (SEQ ID NO: 2) | LTQPHSVSES LGKTVTISC (SEQ ID NO: 10) |
| CDR1 | DYPVN (SEQ ID NO: 3) | TRAGGRIASN YVQ (SEQ ID NO: 11) |
| FR2 | WFRQAPGKGL EWGL (SEQ ID NO: 4) | WYQQRPGSSP TTVIY (SEQ ID NO: 12) |
| CDR2 | IVRSRLYGGT LQYAASVEG (SEQ ID NO: 5) | EDNQRPF (SEQ ID NO: 13) |
| FR3 | RFTISRDDSK SIAYLHMNSL KSEDTAVYYC GV (SEQ ID NO: 6) | GVPDRFSGSI DTSSNSASLT ISGLKTEDEA DYYC (SEQ ID NO: 14) |
| CDR3 | PVANIDY (SEQ ID NO: 7) | QSYDSENPWV (SEQ ID NO: 15) |
| FR4 | WGQGTLVTVS SASTKGPSS (SEQ ID NO: 8) | FGGGTKLTVL G (SEQ ID NO: 16) |

---

We claim:

1. A pharmaceutical preparation comprising:
a pharmaceutically acceptable carrier; and
an antibody consisting essentially of;
a heavy chain amino acid sequence of SEQ ID NO: 1; and
a light chain amino acid sequence of SEQ ID NO: 9.

* * * * *